United States Patent [19]
Petrov et al.

[11] Patent Number: 5,519,151
[45] Date of Patent: May 21, 1996

[54] PROCESS FOR PREPARING POLYFLUOROOXETANES

[75] Inventors: Viacheslav A. Petrov; Bruce E. Smart, both of Wilmington, Del.

[73] Assignee: E. I. Du Pont de Nemours and Company, Wilmington, Del.

[21] Appl. No.: 205,927

[22] Filed: Mar. 3, 1994

[51] Int. Cl.$^6$ .................................................. C07D 305/08
[52] U.S. Cl. ............................................ 549/510; 549/511
[58] Field of Search ...................................... 549/510, 511

[56] References Cited

U.S. PATENT DOCUMENTS

| 2,999,884 | 9/1961 | Weinmayer | 260/633 |
| 3,164,610 | 1/1965 | Davis | 260/333 |

FOREIGN PATENT DOCUMENTS 150055  7/1985  European Pat. Off. .

OTHER PUBLICATIONS

Harris, J. F. et al, *J. Am. Chem. Soc.*, 84, pp. 1553–1561 (1962).

Cook, E. W. et al, *J. Heterocycl. Chem.*, 2, pp. 327–328 (1965).

Belen'kii, G. I. et al, *Bull. Acad. of Science, USSR Chem. Div.*, pp. 1248–1250 (1978).

Weinmayer, V., *J. Org. Chem.*, 28 pp. 492–494 (1963).

*Primary Examiner*—C. Warren Ivy
*Assistant Examiner*—Ba K. Trinh

[57] ABSTRACT

This invention concerns a process for the preparation of polyfluorooxetanes by the reaction of fluoroketones or fluoroepoxides with haloethylenes in the presence of a Lewis acid catalyst. Polyfluorooxetanes are useful as solvents and plasticizers having high thermal stability.

15 Claims, No Drawings

PROCESS FOR PREPARING POLYFLUOROOXETANES

FIELD OF THE INVENTION

This invention concerns a process for the preparation of polyfluorooxetanes by the reaction of fluoroketones or fluoroepoxides with haloethylenes. Polyfluorooxetanes are useful as solvents and plasticizers having high thermal stability.

TECHNICAL BACKGROUND

French patent No. 1,391,493 discloses polyfluorooxetanes of the formula

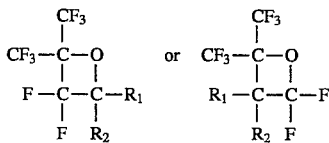

where $R_1$ and $R_2$ is hydrogen, chlorine or fluorine. The utility of said compounds is as chemical intermediates, solvents and plasticizers characterized by a high degree of thermal stability and inertness. The polyfluorooxetanes are prepared by the photochemical reaction between fluoroketones and fluoroolefins.

J. F. Harris, D. D. Coffman, J. Am. Chem. Soc., 84, 1553 (1962) and E. W. Cook, B. F. Landrum, J. Heterocycl. Chem., 2, 327 (1965) disclose similar processes and tabulate a large number of polyfluorooxetanes prepared by this route. Such processes proceed only under UV irradiation, which significantly limits productivity and makes it difficult to use them for preparation of the compounds on a commercial scale.

U.S. Pat. No. 3,164,610 discloses the preparation of partially fluorinated oxetanes by the non-catalyzed reaction of fluorinated ketones with non-fluorinated vinyl ethers. Only highly reactive non-fluorinated vinyl ethers may be involved in the reaction.

G. G. Belen'kii, G. I. Savicheva, E. P. Lur'e, L. S. German, Bull. Acad. of Science USSR. Chem. Div., 1248 (1978) disclose the reaction of trifluorotrichloro-acetone with tetrafluoroethylene in the presence of antimony pentafluoride to give a 45% yield of a mixture comprising an open chain ketone, 1,1,4,4,5,5,5-hepta-fluoro-1,3,3-trichloro-2-pentanone (36%) and an oxetane, 2-difluorochloromethyl-2-dichlorofluoromethyltetra-fluorooxetane (64%). Also disclosed is the reaction of the same substituted acetone with trifluoroethylene in the presence of antimony pentafluoride to give a 27% yield of a three component mixture comprising an open chain ketone (22%) and two different oxetanes (67% and 11%, respectively).

U.S. Pat. No. 2,992,884 discloses the formation of oxetane containing mixtures.

V. Weinmayr, J. Org. Chem. 28, 492(1963) discloses the reaction of tetrafluoroethylene with bis (fluoro-methyl) ether (formed in situ from formaldehyde and HF) to give fluoromethyl-2,2,3,3,3-pentafluoropropyl ether and/or 2,2,3, 3,3-pentafluoro-1-propanol depending on temperature in addition to 4 small quantity by-products one of which is 2,2,3, 3-tetrafluorooxetane.

SUMMARY OF THE INVENTION

This invention provides a process for the preparation of polyfluorooxetanes which process comprises the reaction of fluoroketones or fluoro-epoxides with haloolefins in the presence of a Lewis acid catalyst. Suitable catalysts are selected from aluminum chlorofluoride ($AlF_nCl_{3-n}$), wherein n is from 0 to 2.95, or metal fluorides which do not possess oxidative properties, such as $NbF_5$ or $TaF_5$. The process can be carried out in the optional presence of an inert solvent.

DETAILED DESCRIPTION OF THE INVENTION

Polyfluorooxetanes are prepared by the reaction of hexafluoroacetone (HFA) and other fluoroketones or fluoroepoxides with fluoro, chloro, or bromoethylenes within a temperature range 100°–150° C. The reaction is catalyzed by strong Lewis acids, such as aluminum chlorofluoride $AlF_nCl_{3-n}$ wherein n is 0 to 2.95, or metal fluorides which do not posses oxidative properties. Examples of such metal fluorides are $NbF_5$, and $TaF_5$. In most cases, oxetane product is obtained as a single regioisomer.

Ketones useful herein are of the formula

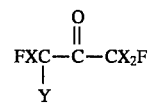

wherein X is F or Cl and Y is selected from the group consisting of F, Cl, and $R_f(C_1–C_5)$, where $R_f$ is a perfluoroalkyl radical and $C_1$ to $C_5$ indicates that it has one to five carbon atoms, optionally containing ether oxygen and terminal functional groups such as —CN, $C_6F_5O$—, —C(O)F, $SO_2F$ and C(O)R', wherein R' is $C_1$ to $C_5$ alkyl or phenyl.

Epoxides useful herein are of the formula $CF_2OCFCFXY$, wherein X is F or Cl and Y is selected from the group consisting of F, Cl, and $R_f(C_1–C_5)$, where $R_f$ is a perfluoroalkyl radical and $C_1$ to $C_5$ indicates that it has one to five carbon atoms, optionally containing ether oxygen and terminal functional groups such as —CN, $C_6F_5O$—, —C(O)F, $SO_2F$ and C(O) R', wherein R' is $C_1$ to $C_5$ alkyl or phenyl. The most preferred epoxide is hexafluoropropylene oxide (HFPO).

Olefins useful herein are of the formula $CX'_2=CY'Z'$, wherein X' is F or Cl and Y' and Z' are independently H, Cl, Br, F, $R_f(C_{1-C3})$, $OR(C_1–C_3)$, where R is $C_1$ to $C_3$ alkyl, provided that only one of Y' and Z' is $R_f(C_1–C_3)$, Br or Cl. Preferred olefins herein include $CHBr=CF_2$, $CHCl=CF_2$, $CFH=CF_2$, $CF_2=CF_2$, $CF_2=CFCl$, $CH_2=CCl_2$, $CH_2=CF_2$, $CF_2=CFBr$. Most preferred are $CF_2=CFH$, $CF_2=CF_2$, $CClH=CF_2$ and $CBrH=CF_2$.

The reaction is carried out in the presence of strong Lewis acid catalysts, such as aluminum halides, wherein the halide is one or more of F, Cl, Br or I, with a proviso that the halide cannot be entirely F. Active catalysts can be preformed, as in most examples below, or can be formed in situ by partial halogen-F exchange. Preferred catalysts are of the structure $AlF_nCl_{3-n}$, where n is from 0 to 2.95. Fluorinated $AlCl_3$ catalyst can be prepared by the reaction of $AlCl_3$ and $CFCl_3$, as described in U.S. Pat. No. 5,162,594, column 4, lines 35–57, which is incorporated herein by reference, in its entirety.

The proportion of catalyst to olefin or ketone is 0.1–0.2 mol per mol of olefin or ketone; the proportion of ketone to olefin is 1:1.

The reaction temperature is about 50° C. to about 200° C., preferably about 100° C. to about 150° C. Reaction times can vary from about one hour to several hours, depending upon such variables as catalyst concentration, pressure and temperature.

Solvents are generally not essential to the reaction but may, optionally, be used if they are relatively inert to the reaction conditions. By "relatively inert" is meant substantially unreactive toward the catalyst at reaction temperatures. Relatively inert materials that can be used as solvents include perhalogenated or highly fluorinated linear and cyclic alkanes and ethers.

Products of this process have the following structure:

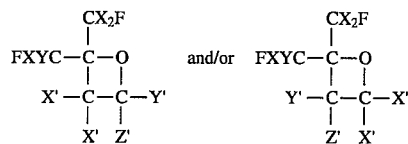

X' is F or Cl and Y' and Z' are independently H, Cl, Br, F, $R_f(C_{1-C3})$, $OR(C_1-C_3)$, where R is $C_1$ to $C_3$ alkyl, provided that only one of Y' and Z' is $R_f(C_1$ to $C_3)$, Br or Cl; and wherein X is F or Cl and Y is selected from the group consisting of F, Cl, and $R_f(C_1-C_5)$, optionally containing ether oxygen and terminal functional groups such as —CN, $C_6F_5O$—, —C(O)F, —$SO_2F$ and C(O)R', wherein R' is $C_1$ to $C_5$ alkyl or phenyl.

EXAMPLES

Catalyst preparation, $AlCl_3+CFCl_3$ 500 g (3.75 mol) of $AlCl_3$ (Aldrich-99% pure) was stirred mechanically under $N_2$ in a r.b. flask fitted with a $-80°$ C. condenser while 1750 mL (about 2625 g, 19 mol) of $CFCl_3$ was added over a 1.5 hr period. Reaction is very exothermic in the early stages, so addition of $CFCl_3$ was slow at first in order to keep the temperature below 65° C., then rapid The resulting suspension was stirred an additional 3 hrs while volatiles ($CF_2Cl_2$) were allowed to escape through the warmed condenser. The condenser was then replaced with a simple stillhead, and most of the $CCl_4$ was distilled under reduced pressure [mainly bp 38° C. (200 mm)]. Finally, the last traces of volatiles were removed by warming the residual solid to 30°–35° C. at 0.05 mm.

The sealed round bottom flask was transferred to a dry box and unloaded into a Teflon®FEP bottle; 340 g of rather finely divided yellow-green solid. Portions of the catalyst were weighed out in the dry box as needed and taken out in plastic bottles with pressure-seal caps.

Analysis for fluorine of the products from preparation of this type indicated the composition to be $AlF_{2.9}Cl_{0.1}$, $AlF_nCl_{(3-n)}$; n=2.9.

EXAMPLE 1

A 400 ml Hastelloy shaker tube was loaded with 2 g of aluminum chlorofluoride (ACF—prepared by reaction of $CFCl_3$ and $AlCl_3$), cooled to $-78°$ C., evacuated and charged with 51 g (0.31 mol) of hexafluoroacetone (HFA) and 24 g (0.3 mol) of trifluoroethylene. The reaction vessel was shaken at 100° C. for 18 h. The mixture of starting materials and products was bled out of the reactor at 40°–50° C. and collected in a cold trap ($-78°$ C.). Starting materials were distilled out on a low temperature distillation column, and the residue was washed with cold water to remove residual HFA, dried over $P_2O_5$ and distilled to give 47 g (64% isolated yield, 100% yield on converted HFA and trifluoroethylene ) of F-2,2 -dimethyl -3 -H-oxetane with b.p. 44°–45° C .

EXAMPLE 2

Following the procedure of Example 1, 70 g (0.42 mol) HFA, 5 g of ACF and 40 g (0.4 mol) tetra-fluoroethylene (TFE) was shaken at 60° C. for a total reaction time of 48 h (TFE was loaded in two portions: 20 g initially and 20 g after 24 h) . After isolation as in Example 1, there was obtained 70 g (100% yield based on the HFA that was converted) of F-2,2-dimethyloxetane, b.p. 27°–28° C. and 10 g of polytetrafluoroethylene, identified by IR. F-2,2-dimethyloxetane: $^{19}F$: −78.88 (6F, t), −79.53 (2F, br.s.) −118.70 (2F, hept), J=9Hz, MS (m/z): 265.9785 ($M^+$, $C_5F_{10}O^+$, calc. 265.9789). Coversion of HFA was 66%.

EXAMPLE 3

In the procedure of Example 1, 40 g (0.24 mol) HFA, 29 g (0.2 mol) of $CHBr=CF_2$ and 0.5 g ACF were allowed to react. The reaction vessel was shaken 18 h at 100° C. The reaction mixture was worked up as in Example 1. There was isolated 20.4 g (100% yield) of F-2,2-dimethyl-3H-3Br-oxetane, b.p. 77°–78° C. $^1H$ NMR: 5.25 (t). Conversion of HFA and olefin was 30%.

EXAMPLE 4

In the procedure of Example 1, 50 g (0.3 mol) of HFA, 35 g (0.28 mol) of chlorotrifluoroethylene (CTFE) and 3 g of ACF were allowed to react. The reactor was shaken 18 h at 100° C. The reaction mixture was worked up as in Example 1. There was isolated 37 g of liquid, b.p. 55° C. According to GC and $^{19}F$ data the product was 42% of F-2,2-dimethyl-3-chlorooxetane, 48% of F-2,2-dimethyl-4-chlorooxetane and 10% of 1,2-dichloro-hexa-fluorocyclobutane. Calculated yield of oxetanes was 82% based on coverted CTFE, conversion of HFA was 43%. Conversion of CTFE was 48%.

EXAMPLE 5

As in Example 1, 50 g (0.3 mol) of HFA, 45 g (0.28 mol) of bromotrifluoroethylene and 0.5 g of ACF were allowed to react. The reactor was shaken 18 h at 100° C. The reaction mixture was worked up as above. There was isolated 12 g of liquid, b.p. 67°–68° C. According to $^{19}F$ NMR the product was a mixture of 54% of F-2,2-dimethyl-3-bromorooxetane and 46% of F-2,2-dimethyl-4-bromooxetane. The yield of oxetanes was 70% based on converted HFA, conversion of HFA and olefin was 18%.

EXAMPLE 6

As in Example 1, 50 g (0.3 mol) of HFA, 25 g (0.39 mol) of 1,1-difluoroethylene and 5 g of ACF were allowed to react. The reactor was shaken 18 h at 100° C. The reaction mixture was worked up as above. There was isolated 25 g of liquid, which was according to GC and $^{19}F$ was a mixture of 75% of F-2,2-dimethyl-3,3-dihydro-oxetane, 20% of F-2-hydro-3-hydroxy-3-trifluoromethyl-butene-1 and 5% of F-2,2-dihydro-3-hydroxy-3-trifluoro-methyl-butane. Washing this mixture with a 10% aqueous solution of NaOH gave pure oxetane, b.p. 55°–55.5° C. $^{19}$ F NMR ($CDCl_3$): −60.23 (6F, m), −78.29 (2F, t); $^1H$ NMR: 3.46 (t) . Calculated yield of oxetane was 82% based on converted HFA, conversion of HFA and olefin was 33%.

EXAMPLE 7

As in Example 1, 50 g (0.3 mol) of HFA, 29 g (0.3 mol) of 1,1-dichloroethylene (freshly distilled, without a stabilizer) and 5 g of ACF were allowed to react. The reactor was shaken 18 h at 100° C. The reaction mixture was worked up as above. There was isolated 16 g of liquid with b.p. 100°–103° C. which was according to GC/MS and $^{19}$F NMR a mixture of 90% of F-2,2-dimethyl-3,3-dihydro-4,4-dichloro-oxetane and 10% of 2-hydro-3-hydroxy-3-trifluoromethyl-1, 1-dichloro-butene-1. Calculated yield of oxetane was 80% based on converted HFA, conversion of HFA was 20%.

EXAMPLE 8

As in Example 1, 70 g (0.42 mol) of HFA, 40 g (0.41 mol) of 1-hydro-1-chloro-2,2-difluoroethylene, (containing 10% of isomeric 1-hydro-2-chloro-1,2-difluoroethylene), and 5 g of ACF were allowed to react. The reactor was shaken 18 h at 100° C. The reaction mixture was worked up as above. There was isolated 2.6 g of liquid, b.p. 62°–64° C. According to GC/MS and $^{19}$F NMR the product was a mixture of 90% of F-2,2-dimethyl-3-chloro-3-hydro-oxetane and 10% of F-2,2-dimethyl-3-hydro-4-chlorooxetane (mixture of diastereomers). Calculated yield (GC) of oxetanes was 91% based on converted HFA; conversion of HFA was 22%.

EXAMPLE 9

As in Example 1, 37 g (0.2 mol) of chloropenta-fluoroacetone, 3 g of ACF and 20 g (0.2 mol) of TFE were allowed to react. The reaction vessel was shaken 18 h at 60° C. There was isolated 5.8 g of F-2-chloromethyl-2-methyloxetane. Yield was 9.8%.

EXAMPLE 10

As in Example 1, 18 g (0.1 mol) of chloropenta-fluoroacetone, 5 g of ACF and 7 g (0.11 mol) of $CH_2=CF_2$ were allowed to react. The reaction vessel was shaken 18 h at 100° C. There was isolated 8 g of a mixture of 75% of F-2-chloromethyl-2-methyloxetane and 25% of unidentified material. Calculated yield of oxetane (GC) was 24.4%.

EXAMPLE 11

As in Example 1, 20 g (0.12 mol) of HFA, 3 g of $AlCl_3$ and 9 g (0.11 mol) of trifluoroethylene were allowed to react. The reaction vessel was shaken 18 h at 100° C. There was isolated 3 g of F-2-dimethyl-3-H-oxetane, 80% purity. The yield of oxetane was 8.3 %.

EXAMPLE 12

As in Example 1, 50 g (0.3 mol) HFPO, 5 g ACF and 25 g (0.25 mol) TFE was allowed to react at 60° C. for 48 h. (TFE was loaded in two portions: 15 g initially and 10 g after 24 h.) There was isolated 15 g (100% on converted HFPO) of F-2,2-dimethyloxetane, and 4 g polytetrafluoroethylene. Conversion of TFE was 38%.

EXAMPLE 13

As in Example 1, 51 g (0.31 mol) HFPO, 5 ACF and 24 g (0.375 mol) $CH_2=CF_2$ was allowed to react at 100° C. for 18 h. There was isolated 20.4 g of a mixture, containing 73% of F-2,2-dimethyl-3,3-dihydrooxetane, 18% of F-2-hydro-3-hydroxy-3-trifluoromethyl-butene-1 and 9% of F-2,2-dihydro-3-hydroxy-3-trifluoromethylbutane. The yield of oxetane was 73%, based on converted HFPO.

What is claimed is:

1. A process for the preparation of a polyfluorooxetane, comprising contacting a fluoroketone or a fluoroepoxide with a haloolefin in the presence of one or more Lewis acid catalysts, in the optional presence of a solvent wherein the catalyst is selected from aluminum chlorofluoride and aluminum bromofluoride.

2. The process of claim 1 wherein the catalyst is selected from the group consisting of $AlF_nCl_{3-n}$ and $AlF_nBr_{3-n}$, wherein n is 0 to 2.95.

3. The process of claim 1 wherein the ketone is of the formula

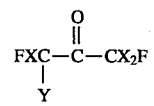

wherein X is F or Cl and Y is selected from the group consisting of F, Cl, $R_f(C_1-C_5)$, $R_f(C_1-C_5)$ containing ether oxygen, —CN, $C_6F_5O$—, —C(O)F, —$SO_2$F and C(O))R' wherein R' is $C_1$ to $C_5$ alkyl or phenyl.

4. The process of claim 1 wherein the haloolefin is of the formula $CX'_2=CY'Z'$, wherein X' is F or Cl and Y' and Z' are independently selected from the group consisting of H, Br, Cl, Br, F, $R_f(C_1-C_3)$, $OR(C_1-C_3)$, where R is $C_1$ to $C_3$ alkyl, provided that only one of Y' and Z' is $R_f(C_1$ to $C_3)$, Br or Cl.

5. The process of claim 4 wherein the haloolefin is selected from the group consisting of $CHBr=CF_2$, $CHCl=CF_2$, $CFH=CF_2$, $CF_2=CF_2$, $CF_2=CFCl$, $CH_2=CCl_2$, $CH_2=CF_2$, $CF_2=CFBr$.

6. The process of claim 5 wherein the haloolefin is selected from the group consisting of $CF_2=CFH$, $CF_2=CF_2$, $CClH=CF_2$ and $CBrH=CF_2$.

7. The process of claim 1 wherein the proportion of ketone to olefin is 1:1.

8. The process of claim 1 wherein the proportion of catalyst to olefin or ketone is 0.1–0.2 mol per mol of olefin or ketone.

9. The process of claim 1 wherein the catalyst is $AlF_nCl_{3-n}$, wherein n is from 0 to 2.95.

10. The process of claim 1 wherein the temperature is within the range about 50° C. to about 200° C.

11. The process of claim 10 wherein the temperature is about 100° C. to about 150° C.

12. The process of claim 1 carried out in the presence of an inert solvent.

13. The process of claim 1 wherein the solvent is selected from polyfluorooxetane of the structure:

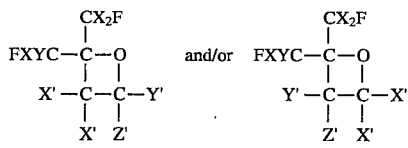

X' is F or Cl and Y' and Z' are independently H, Cl, Br, F, $R_f(C_1-C_3)$, $OR(C_1-C_3)$, where R is $C_1$ to $C_3$ alkyl, provided that only one of Y' and Z' is $R_f(C_1$ to $C_3)$, Br or Cl; and wherein X is F or Cl and Y is selected from the group consisting of F, Cl, and $R_f(C_1-C_5)$, optionally containing ether oxygen and terminal functional groups selected from the group consisting of —CN, $C_6F_5O$—, —C(O)F, —$SO_2$Fm and C(O)R', wherein R' is $C_1$ to $C_5$ alkyl or phenyl.

14. Process of claim 1 wherein the fluoroepoxide is of the formula $CF_2OCFCFXY$, wherein X is F or Cl and Y is selected from the group consisting of F, Cl, and $R_f(C_1-C_5)$, where $R_f$ is a perfluoroalkyl radical optionally containing ether oxygen and terminal functional groups selected from —CN, $C_6F_5O$—, —C(O)F, $SO_2F$ and C(O)R', wherein R' is $C_1$ to $C_5$ alkyl or phenyl.

15. Process of claim 14 wherein the fluoroepoxide is HFPO.

* * * * *